June 19, 1973 H. KERRIGAN Plant Pat. 3,364
AZALEA PLANT
Filed Oct. 18, 1971
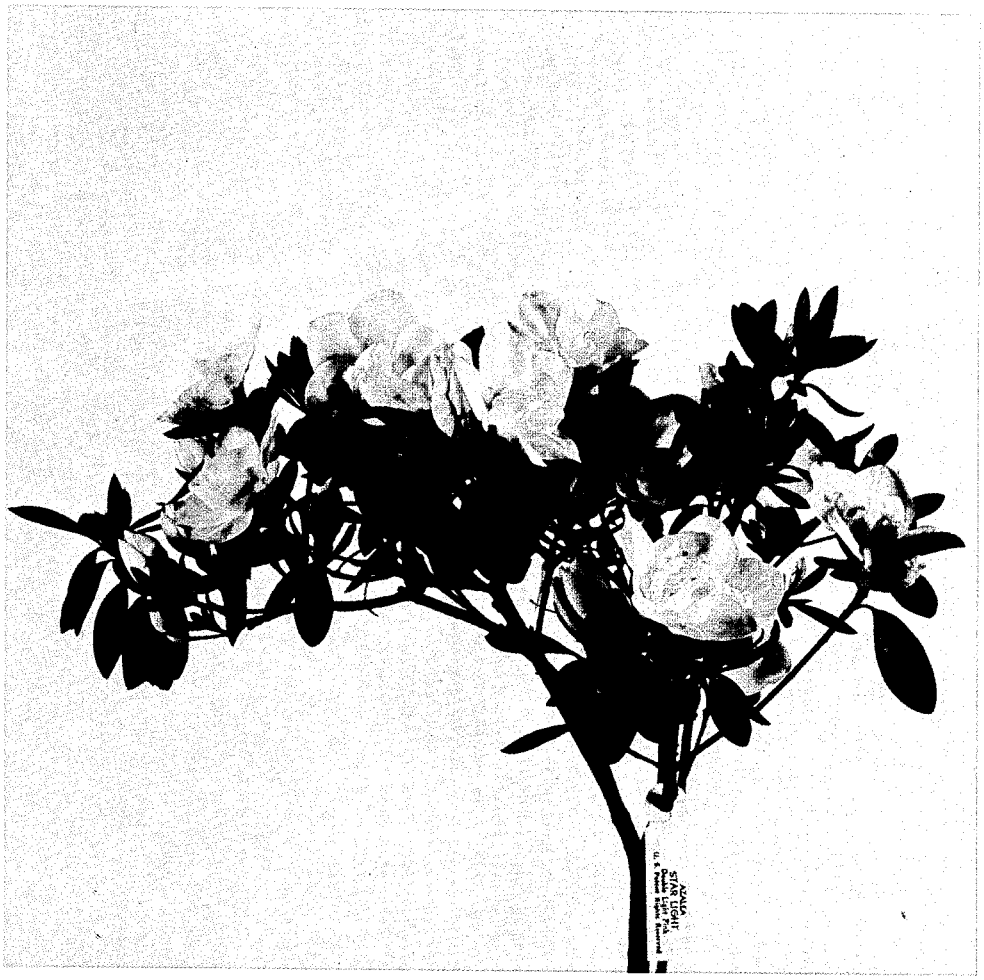

United States Patent Office

Plant Pat. 3,364
Patented June 19, 1973

3,364
AZALEA PLANT

Howard Kerrigan, 25783 Mission Blvd.,
Hayward, Calif.

Filed Oct. 18, 1971, Ser. No. 190,239
Int. Cl. A01h *5/00*
U.S. Cl. Plt.—56 1 Claim This invention relates to a new and distinct variety of azalea plant of the Belgian Indica type.

This new variety of azalea plant has been obtained as a result of a deliberate hybridization program carried out by me in Alameda County, Calif., and was obtained by crossing "Lydia Haerens," female parent, and "Ballerina" (Patent 1,881) male parent.

This new variety of azalea plant does not closely resemble either parent and the particular combination of characteristics present in the variety are essentially new in florists' azaleas. It uniquely possesses large, long-lasting, star shaped soft pink flowers that are exceptionally freely produced on a vigorous bushy plant.

This variety has been found to retain its distinctive characteristics when propagated asexually by means of softwood cuttings for several successive generations in Alameda County, Calif.

The following is a detailed description of my new variety of azalea plant. The color designations are those employed in the Horticultural Colour Chart issued by Wilson Colour Ltd. in collaboration with the Royal Horticultural Society.

The plant characteristics are as follows: As to form, the plant is bushy; as to growth, it is vigorous. The blooming habit is very prolific. The season is February 1 through April 1 and suitability for forcing is excellent.

The foliage characteristics are as follows:

Color: Deep green top, light green bottom; glossy.
Shape: Oblanceolate to obovate.
Size: 1½ inches to 2¼ inches by ⅞ inches by 1⅛ inches.
Texture: Normal.
Ribs & veins: Light green, impressed; midrib mucronate.
Pubescence: Scattered, appressed hairs soft grey when young, aging to brown.
Edge: Entire.

The flower characteristics are as follows:

Size: 4 inches wide, star shaped.
Inflorescence: Usually 1–3 per bud.
Quantity: Abundant.
Form: Semi-double; 6 variable petaloids (anthers aborted, attached); flat (star like).
Texture: Firm, long-lasting.
Color: Dawn Pink 523 shading to 523/2; partial light blotch of magenta 27/2 on upper petaloids.
Ovary: Normal, 5 celled.

I claim:

1. A new and distinct variety of azalea plant of the florists' forcing type, substantially as illustrated and described herein and characterized primarily by its unique four inch wide, soft pink star-shaped flowers, which are reliably produced in unusual profusion on a bushy vigorous plant with a long forcing season.

No references cited.

ROBERT E. BAGWILL, Primary Examiner